United States Patent
Ben-Arye

(10) Patent No.: US 11,849,917 B2
(45) Date of Patent: *Dec. 26, 2023

(54) DISPOSABLE MINIATURE ENDOSCOPY SYSTEM

(71) Applicant: EYELUM LTD., Zichron Yaakov (IL)

(72) Inventor: Asaf Ben-Arye, Zichron Yaakov (IL)

(73) Assignee: EYELUM LTD., Zichron Yaakov (IL)

( * ) Notice: Subject to any disclaimer, the term of this patent is extended or adjusted under 35 U.S.C. 154(b) by 650 days.

This patent is subject to a terminal disclaimer.

(21) Appl. No.: 16/645,475

(22) PCT Filed: Sep. 12, 2018

(86) PCT No.: PCT/IL2018/051026
§ 371 (c)(1),
(2) Date: Mar. 8, 2020

(87) PCT Pub. No.: WO2019/049159
PCT Pub. Date: Mar. 14, 2019

(65) Prior Publication Data
US 2020/0214543 A1    Jul. 9, 2020

Related U.S. Application Data

(60) Provisional application No. 62/556,516, filed on Sep. 11, 2017.

(51) Int. Cl.
*A61B 1/00* (2006.01)
*A61B 1/015* (2006.01)
(Continued)

(52) U.S. Cl.
CPC ...... *A61B 1/00096* (2013.01); *A61B 1/00066* (2013.01); *A61B 1/00082* (2013.01);
(Continued)

(58) Field of Classification Search
CPC ............ A61B 1/00018; A61B 1/00066; A61B 1/00082; A61B 1/00096; A61B 1/00108;
(Continued)

(56) References Cited

U.S. PATENT DOCUMENTS 2,701,559 A * 2/1955 Cooper .................. A61B 10/02
73/864.33
4,800,869 A * 1/1989 Nakajima .......... A61B 1/00068
600/158

(Continued)

FOREIGN PATENT DOCUMENTS

JP    2004029235 A    1/2004
JP    2005124776 A *  5/2005
(Continued)

OTHER PUBLICATIONS

EP Application No. 18853096.8, Extended European Search Report dated Apr. 28, 2021, 6 pages.

(Continued)

*Primary Examiner* — Aaron B Fairchild
*Assistant Examiner* — Stephen Floyd London
(74) *Attorney, Agent, or Firm* — ALPHAPATENT ASSOCIATES, LTD; Daniel J. Swirsky

(57) ABSTRACT

An endoscope assembly comprising a handle incorporating a liquid reservoir and injection system, a cannula attaching to the handle, and a distally attached miniature imaging head. The imaging head is a transparent tubular shaped body having an essentially closed proximal end, and a tubular wall extending from the closed proximal end to the distal open end of the body. An optical source is attached to the closed proximal end, and its emitted illumination directed into the tubular wall of the body, such that said illumination is partially internally reflected within the tubular wall and is emitted both radially and from the distal open end. The (Continued)

optical source is disposed radially inwards of the outer dimensions of the tubular shaped body. Alternatively, the optical source can be positioned back-to-back with the camera chip. A system is provided for cell collection from the region in which the endoscope is operating.

18 Claims, 6 Drawing Sheets

(51) Int. Cl.
*A61B 1/05* (2006.01)
*A61B 1/06* (2006.01)
*A61B 1/07* (2006.01)
*A61B 1/233* (2006.01)
*A61B 1/307* (2006.01)

(52) U.S. Cl.
CPC .......... *A61B 1/00103* (2013.01); *A61B 1/015* (2013.01); *A61B 1/05* (2013.01); *A61B 1/0676* (2013.01); *A61B 1/07* (2013.01); *A61B 1/233* (2013.01); *A61B 1/307* (2013.01)

(58) Field of Classification Search
CPC . A61B 1/00114; A61B 1/00181; A61B 1/015; A61B 1/018; A61B 1/05; A61B 1/051; A61B 1/0607; A61B 1/0615; A61B 1/0625; A61B 1/0676; A61B 1/12; A61B 10/0283; A61B 10/04; A61B 2010/0216; A61M 1/0003; A61M 1/774; A61M 1/76; A61M 25/0097; A61M 2025/1086; A61M 2025/109; G02B 23/2484
See application file for complete search history.

(56) References Cited

U.S. PATENT DOCUMENTS

| | | | |
|---|---|---|---|
| 6,478,730 B1 | 11/2002 | Bala et al. | |
| 6,863,651 B2 | 3/2005 | Remijan | |
| 7,530,946 B2 | 5/2009 | Hartwick et al. | |
| 7,942,814 B2 | 5/2011 | Remijan | |
| 8,038,602 B2 | 10/2011 | Gill et al. | |
| 8,317,689 B1 | 11/2012 | Remijan et al. | |
| 8,708,896 B2 | 4/2014 | Vayser et al. | |
| 8,803,960 B2 | 8/2014 | Sonnenschein et al. | |
| 8,928,746 B1* | 1/2015 | Stevrin | A61B 1/00096 600/109 |
| 9,220,400 B2 | 12/2015 | Petersen et al. | |
| 9,370,295 B2 | 6/2016 | Kienzle et al. | |
| 9,717,398 B2 | 8/2017 | Irion et al. | |
| 10,088,113 B1* | 10/2018 | Chen | G02B 23/2461 |
| 2003/0040658 A1 | 2/2003 | Sano et al. | |
| 2003/0227547 A1* | 12/2003 | Iddan | A61B 1/00096 348/E5.029 |
| 2004/0064018 A1* | 4/2004 | Dunki-Jacobs | A61B 1/07 600/178 |
| 2006/0068360 A1 | 3/2006 | Boulais | |
| 2006/0184084 A1 | 8/2006 | Saadat | |
| 2006/0276692 A1* | 12/2006 | Kucklick | A61B 1/317 600/175 |
| 2009/0054805 A1* | 2/2009 | Boyle, Jr. | A61B 18/14 600/564 |
| 2011/0295061 A1 | 12/2011 | Haramaty et al. | |
| 2012/0253115 A1* | 10/2012 | Erin | A61B 10/04 600/104 |
| 2013/0041356 A1* | 2/2013 | Smith | A61B 1/128 606/13 |
| 2013/0046142 A1 | 2/2013 | Remijan et al. | |
| 2014/0031834 A1 | 1/2014 | Germain et al. | |
| 2014/0107496 A1* | 4/2014 | Hellstrom | A61B 5/0086 600/478 |
| 2014/0210976 A1* | 7/2014 | Lin | G02B 23/2476 348/68 |
| 2014/0221740 A1 | 8/2014 | Kawula et al. | |
| 2014/0276199 A1 | 9/2014 | O'Sullivan et al. | |
| 2018/0063387 A1* | 3/2018 | Wei | A61B 1/00016 |
| 2019/0064079 A1* | 2/2019 | Safai | G02B 27/0075 |
| 2019/0246027 A1* | 8/2019 | Kuhn | A61B 1/051 |
| 2019/0350605 A1* | 11/2019 | Sakurazawa | A61B 17/29 |
| 2021/0022588 A1* | 1/2021 | Schultheis | B29C 45/14426 |
| 2021/0037169 A1* | 2/2021 | Numasawa | A61B 1/0676 |
| 2022/0061645 A1* | 3/2022 | Jochumsen | A61B 1/0011 |

FOREIGN PATENT DOCUMENTS

| | | | | |
|---|---|---|---|---|
| JP | 2005124776 A | 5/2005 | | |
| WO | WO-2012060932 A2 * | 5/2012 | ......... | A61B 1/00034 |
| WO | 2017158597 | 9/2017 | | |

OTHER PUBLICATIONS

EP Application No. 18853096.8, Examination Report dated Jan. 31, 2022, 4 pages.

* cited by examiner

DISPOSABLE MINIATURE ENDOSCOPY SYSTEM

FIELD OF THE INVENTION

The present invention relates to miniature endoscopic devices, that combine an integrated liquid container and irrigation system, and an imaging optical system with a head mounted LED source illuminating the field of view by means of a light guide.

BACKGROUND

Endoscopy is used for the inspection of internal organs, by means of insertion of visualization devices into the body through small incisions or through natural orifices. Typically, endoscopes are comprised of a camera and its associated optical system, a light source, as well as irrigation and working channel. Many flexible endoscopy devices also include a mechanical navigation component.

Small diameter endoscopes are used to penetrate into small anatomical cavities or thin tubal structures, such as in the nose, urinary system, or within bone joints. Miniature endoscopes having a diameter in the range of 1.8 mm, or less, are required for inspection of organs with very small diameter lumens, such as the fallopian tubes, or to enhance the availability of visualization means, through minimally invasive incisions, sometimes no larger than a large needle insertion, such as for inspection of joints and small cavity organs. The use of such miniature endoscopes can enable performance of direct and immediate visualization of organs, in an office setting, thereby avoiding costly imaging methods, such as MRI or CT. An important requirement for enabling the availability of such devices to more clinicians is a small device having low manufacturing costs, which enables the entire endoscope to be disposable, if desired.

Most current endoscopy systems use LED illumination fiber optically transmitted from the proximal end, or from a LED mounted on the tip of the endoscope. Such prior art illumination arrangements disadvantageously increase the diameter of the endoscope beyond the diameter dictated by the camera, camera housing, and optical imaging system. Some endoscopes have one or more illumination fibers or fiber bundles at or near the outer surface of the endoscope, and in order to provide enough illumination output, these fibers may be large, thereby increasing the total endoscope diameter. In U.S. Pat. No. 9,370,295, to R. A. Kienzle et al, for "Fully Integrated, Disposable Tissue Visualization Device", for example, there are multiple illumination fibers or fiber bundles surrounding the image guide, and the diameter is further increased by an infusion lumen and an outer tubular body. In JP 2005124776A to CHINONTEC K K, the system has a lens holder formed of a material that does not transmit the illumination light. The use of such a lens holder generally increases the diameter of the endoscope head. Other endoscope designs incorporate a light source at the proximal end of the endoscope and a sheath acting as a waveguide spanning the entire length of the endoscope such as is shown in U.S. Pat. No. 6,478,730 to J. L. Bala et al, for "Zoom Laparoscope". This sheath increases the diameter of the entire length of the endoscope beyond what is necessary to house the camera. Such a sheath may also involve additional absorption of light due to the length of transmission, which may reduce the usable illumination. In addition to increasing the diameter of endoscopes, sheath waveguides and fibers that run the entire length of the endoscope increase design complexity and construction costs, reducing disposability and maneuverability. Even in cases where there are no large fibers, sheaths or lens holders that increase the diameter of the endoscope, and only LEDs embedded in the camera housing at the very distal end of the endoscope, such as in U.S. Pat. No. 9,220,400 to L. K. G. Peterson for "Endoscope having a Camera Housing and Method for making a Camera Housing", the LEDs are peripheral to the camera and thus increase the diameter of the endoscope.

Most endoscopes are also connected to a power-supply by an electrical cable, and receive their liquid supply for irrigation from an external irrigation source, such as from dedicated fluid bags, or by means of an irrigation device external to the endoscopy head, such as on a cart. An external irrigation device as described in US 2006/0068360 to D. R. Boulais for "Single Use Fluid Reservoir for an Endoscope" requires a dedicated surface to rest upon and thus decreases maneuverability. It requires additional construction, increasing the cost of the endoscope, and requires a high pressure output to inject fluid, as the device is far from the area to be injected. In a system described in US 2014/0031834 to Germain et al for "Medical Device and Methods", both the fluid source and the pump for ejecting fluid from the fluid source are located on a cart external to the endoscope head that connect to the endoscope via a fluid inflow source on the endoscope handle.

A low cost, disposable endoscope, increases the availability of such a diagnostic modality to more physicians, enabling them to conduct endoscopic examinations in clinics, without the need to purchase and maintain costly endoscopic equipment, which typically includes a floor standing console with control equipment and a reusable endoscope requiring cleaning and sterilizing. In addition, low diameter endoscopes required for viewing small lumens, are hard to re-process, thus increasing the probability of contamination when re used.

Furthermore, the diameter limitations of prior art endoscopes are problematic for many applications on small diameter lumens or small organs, and there therefore exists a need for a miniature, small diameter, simple construction disposable endoscope, which provides adequate light and efficient light distribution over the area of interest, and fluid output, while overcoming at least some of the disadvantages of prior art systems and methods. The miniature endoscope devices described in International Patent Application PCT/IL2017/050320, having a common inventor with the present Application, may have light distribution patterns resembling a Gaussian function and may thus provide a disproportional amount of illumination to the central region of the area to be illuminated. This may result in difficulties in imaging the peripheral field of view of the endoscope, or alternatively, of the possibility of causing thermal damage to the central region if the illumination is increased. There therefore exists the need for a miniature endoscope with more uniform and controllable illumination distribution.

The disclosures of any publications mentioned in this section and in other sections of the specification, are hereby incorporated by reference, each in its entirety.

SUMMARY

The present disclosure describes new exemplary systems for miniature endoscopes, having a simple construction, and a small outer diameter while still providing adequate imaging, light and fluid output. An efficient distribution of light is emitted such that the entire area to be imaged receives adequate illumination and that no areas are over illuminated.

Such systems have a handle at the proximal end of the endoscope, a rigid or flexible cannula extending from the handle to the head, and an imaging head incorporating the illumination source at the distal end of the cannula. The term distal throughout this disclosure means the portion of the device which is closest to the patient or subject, and proximal is used to describe the portion of the device which is closest to the user, such as a doctor.

In a particularly advantageous implementation, the imaging head uses at least one LED as its illumination source, located in the proximal end of the endoscope head in such a position that it does not extend beyond the largest radial dimension of the imager and its housing. The proximal end of the endoscope head where the illumination source is located may be completely or mostly closed, and may be tapered such that there is a reduction in the diameter as compared to the distal end of the endoscope head. Positioning of this light source within and not larger than the outer diameter of the lens holder in the endoscope head enables the maintenance of a diameter no larger than that of the imager. The illumination source emits light into an illumination guide in the outer portion of the imaging head. This illumination guide avoids the need for long optical fibers and enables a more maneuverable, low diameter and low cost endoscopy system. The illumination source, usually one or more LEDs is located behind the imaging sensor, and white light emitting LEDs usually provide the most natural illumination.

Furthermore, such an imaging head comprises a lens assembly, generally having at least two lenses to provide sufficient imaging quality. Unlike prior art systems that comprise a separate lens holder that increases the diameter of the endoscope and does not provide any illumination functionality, in a novel arrangement, the lens assembly is held by direct contact with the illumination guide. Thus the illumination guide, being made of a material that transmits the illuminated light, functions both as a light guide and also as a lens holder to structurally secure the lens assembly in place. To further decrease the diameter of the endoscope, the lens assembly may be produced using wafer level optics, such as with layers of printed lenses on glass substrates, being attached and then cut, forming a module with the lenses already fixed in place.

Light from the illumination source(s) is advantageously emitted in a distribution both radially out of the peripheral walls of the illumination guide and longitudinally out of the distal end of the illumination guide, using partial internal reflection along the walls of the illumination guide. The radially emitted light is either scattered by the outer endoscope surface or is diffused within the tissues radially situated to the endoscope head, or a combination thereof. This scattering or diffusion allows a portion of the radially emitted light to be ultimately directed distally, such that the distribution of light emitted by the endoscope head is not limited to that resembling a Gaussian function, with a disproportionate amount of the light reaching the central portion of the area to be illuminated.

Such a distribution may be predetermined to provide proportions of distally and radially emitted light that result in a large intensity of light and good illumination of the area of examination. The illumination source(s) may be positioned at a predetermined pose such that the angles of incidence of its emitted light result in such a predetermined distribution. Alternatively or additionally, the walls of the illumination guide are constructed to have a predetermined reflectivity or known diffusive properties that will generate these distribution effects. This arrangement results in a more widely spread distribution of light and in adequate illumination to the entire area to be imaged.

Endoscopy devices need irrigation means to help open their path along the investigated organ or lumen, and to clean that region to be viewed. This irrigation is generally performed in the prior art by external connection from a liquid reservoir, through a tube or set of tubes into the endoscope, creating a cumbersome structure that may limit operator/surgeon flexibility during the procedure. In contrast, the small diameter devices described in the present disclosure for insertion into small volume organs, need a lower volume of liquid, and thus can use a relatively small liquid reservoir. In the presently described endoscopes, such a compact reservoir is sufficiently small that both the liquid reservoir and the liquid injection system, comprising a pump, can be contained entirely in the volume of the handle at the proximal end of the endoscope. Although this is the most compact structure, in an alternative implementation, the liquid reservoir, such as saline or glucose solution liquid bag, may be located outside of the handle and may be connected by tube to the handle of the miniature endoscope system. A reservoir that is within the handle and not external to the whole endoscope device may be closer to the distal end of the endoscope, and thus require a lower pressure input to cause the liquid to flow from the reservoir to the region to be cleaned. Such an integrated reservoir contributes to the low construction cost and disposability of the entire endoscope device, reducing risk of contamination to the patient. The handle may contain an integrated injection mechanism, either hand operated by the user, though optionally electrically powered, injecting liquid from the reservoir along the flexible cannula of the endoscope towards the distal end of the device, where it is discharged into the organ or lumen through an irrigating opening(s). Such a function is effective for the small diameter endoscopes described in the present disclosure, because of the small quantities of fluid required.

Images from the camera may also be transmitted by means of a wireless connection link, to save the need for additional signal cables back to the home console, thereby providing more flexibility to the user and avoiding cumbersome maneuverability. However, the advantage of wireless connection may be offset by the added cost. The LED light source(s) can be powered by a battery, which can conveniently be located in the operator's handle of the device, and connected to the LED source(s) either by wires or by printed conductors along the walls of the cannula shaft of the endoscope. For suitably miniaturized batteries, the batteries may be installed on board the endoscope head.

In an alternative implementation, the endoscope head is constructed with the illumination source directing its illumination in a proximal direction, and the illumination is reflected by the curved proximal surface of the head distally down the optical guide to illuminate the field of view. The image information from the detector array is modulated onto the illumination, and a sample of that illumination is transmitted directly optically back down the endoscope, where the image information is demodulated from the illumination sample and is used for display of the image. Another advantage of this construction is that the operating circuitry of the illumination source, and of the detector array are back-to-back, and can thus be electrically connected, thereby saving separate supply of power to these two components, and enabling simple interaction between them, such as the modulation of the illumination with the signal data from the display array.

In addition to the irrigation liquid container, the liquid injection mechanism, and the battery and circuitry that provides power to the electronic components of the device, the handle may also contain a wireless transmitter unit for transferring images and data acquired by the imaging system back to a display console, such as a computer screen, a mobile phone or any other designated display.

The size of the exemplary miniature endoscope system enables its entry into very small bodily lumens and requires only a minimal incision, which further reduces risks to the patient. Such a proposed device increases the availability of endoscopy means to more physicians, because it is affordable and enabled in the doctor's office with sterility ensured by one-time use of each disposable device, and low overhead costs. Because of its small overall external diameter, it can be used in lumens and locations having less than 1.8 mm internal dimensions between their walls. This enables it to be used in applications such as in orthopedics, for entry into joints, or in gynecology, such as for detecting blockages in the fallopian tubes. Conventional endoscopes are unable to efficiently enter such small spaces.

The combination of an integrated liquid reservoir and injection mechanism, wireless image transmission and an integrated battery based power supply enable higher maneuverability and flexibility to the user, because there is no need to connect any wires or tubes to an endoscope control console, or to any services provided externally to the endoscope. The devices of the present disclosure are completely self-contained and autonomous. They are not connected to an office-based system with a control unit sitting on a desk, a stand, or on the floor, but are completely hand-held by the doctor. This autonomy and the simple and cost-effective structure allow the presently disclosed devices to be made completely disposable, thereby decreasing the risk of infection, and reducing the cost per procedure. Such a low production cost increases the availability of the device for various applications and medical procedures, such as for Falloposcopy, Ear Nose and Throat applications, Arthroscopy, urology and other minimally invasive surgical procedures.

Furthermore, in an advantageous implementation, the endoscope may additionally be used for sampling cells in a region being investigated by flushing the region with a liquid, and then pumping out the liquid with the cells to be investigated. Such a cytological pump can be used in gynecology, for instance, for the detection of ovarian cancer. Such a cytological analysis must include means of detaching and collecting the cells to be analyzed. The flushing solution containing the cells may be collected in a special reservoir located in the handle of the device. A number of schemes are proposed for performing this collection. In a first implementation, the endoscope may be equipped with an inflatable balloon disposed peripherally to the catheter. Such a balloon may have a rough or toothed external surface, which can be inflated when the endoscope head reaches its desired location, and then the balloon surface scrapes off cells for analysis. A balloon is particularly advantageous because its outer surface conforms to the walls of the anatomical space in which the endoscope is exploring. The inflation pressure may be controlled in order to provide an efficient cell collection procedure without danger of damage to the subject by over-inflation. As an alternative to a balloon, the outer walls of the endoscope head itself may have a structured surface, for example a swab-like surface, such that, for instance, in the case of the fallopian tubes, the structured outer surface collects cells trapped among the cilia or the mucosa on the inner walls of the fallopian tubes. In this implementation, the small diameter of the endoscope head is not increased. Both the balloon and structured surface embodiments allow for simpler methods of cell collection than the prior art method of passing a swab down the working channel of the endoscope.

The miniature endoscopes described in the present disclosure can be used for penetration and visualization of tubal or hollow anatomical organs or small cavities or for penetration through very small, needle-size incisions. Once through the skin or penetrated into its target organ, small liquid injection maneuvers can enhance forward movement of the endoscope tip and can open collapsed tubes, as well as help cleaning the region in front of the camera. Additionally, the endoscope may optionally be directed down a previously inserted guide wire, which can exit the endoscope distally and obliquely through the flushing hole in the distal end of the endoscope. Although the endoscope cannula is shown as a flexible tube in the drawings of this application, thus enabling maneuvering through curving lumens and into locations behind other organs, the endoscope can also be implemented using a rigid shaft connecting the handle with the endoscope imaging head, and this disclosure is intended to apply to such a rigid tube endoscope implementation also.

There is thus provided in accordance with an exemplary implementation of the devices described in this disclosure, an endoscope for insertion into an anatomical space of a subject, comprising:
(i) a handle comprising a liquid reservoir housed entirely in the handle and a liquid injection system comprising a pump,
(ii) a cannula attached at its proximal end to the handle, the cannula having at least one opening through which liquid from the reservoir can be ejected, and
(iii) an imaging head attached to the distal end of the cannula, the imaging head comprising:
   (a) a transparent tubular shaped body having an essentially closed proximal end, and a tubular wall extending from the essentially closed proximal end and terminating at a distal open end of the tubular shaped body,
   (b) at least one light source associated with the essentially closed proximal end such that its illumination is directed into the tubular wall, the at least one light source being disposed radially inwards of the outer dimensions of the tubular shaped body,
   (c) a two dimensional detector array disposed inwardly of the inner surface of the tubular wall and distal to the at least one light source, and
   (d) an imaging lens assembly held by direct contact with the transparent tubular shaped body and positioned distally to the detector array, such that it images onto the detector array, light reflected back into the imaging head,
wherein the imaging head has a structure such that the illumination directed into the tubular wall is emitted partially distally and partially radially therefrom.

In such an endoscope, the pump may be housed entirely in the handle. The pump may be adapted to eject liquid from the reservoir through the cannula and out of the at least one opening in the cannula.

Additionally, the imaging lens assembly and the two-dimensional detector array may be constructed together as a Wafer Level Optics (WLO) assembly.

Furthermore, in any such endoscopes, the partially distally emitted and partially radially emitted illumination from the tubular wall may have a distribution which is adapted to be suitable for the illumination requirements of the anatomical space.

In order to achieve this, the outer surface of the tubular wall may have a partially reflective coating that has a reflectivity chosen to achieve a predetermined proportion of light to be emitted radially and a predetermined proportion of light to be emitted distally. This distribution may be achieved, at least in part, by the pose of the at least one light source. Alternatively, the distribution may be achieved, at least in part, by having optically diffusive coatings on at least parts of the outer surface of the tubular wall.

According to yet other implementations of the endoscopes of this disclosure, the at least one optical source may comprise at least one light emitting diode. Additionally, the tubular wall may be the barrel of the lens assembly. The distal lens of the lens assembly may be designed such that its distal surface is convex shaped such that it reduces trauma to the anatomical space through which the endoscope is passed. Furthermore, the imaging head may be less than 1.8 mm. in diameter and 6 mm. in length.

Other implementations of such endoscopes may further involve a cytological collection element associated with the imaging head, that is adapted to detach cells from the anatomical space in which the imaging head is situated. In such cases, the handle may further comprise a liquid withdrawal mechanism adapted to withdraw liquid in a proximal direction through the catheter, and then, the endoscope may further comprise a cell collection vessel within the handle to collect liquid withdrawn from the liquid withdrawal mechanism.

The cytological collection element may be an inflatable balloon having a rough or toothed or hairy external surface. The balloon may be inflatable by means of a pump. In an alternative implementation, the cytological collection element may be disposed on the end of a guide wire deployed from an irrigation opening in the endoscope cannula wall.

In an alternative implementation, the cytological collection element may be a structured surface on the outer surface of at least one of the tubular wall and at least part of the cannula. In that case, the structured surface may be at least one of (i) rough, (ii) jagged, (iii) toothed, and (iv) hairy.

All such endoscopes are self-contained in that they may be operable without the need for external supplies.

Finally, there is also provided a method of inspecting an anatomical space using an endoscope according to any of the above claims, wherein the anatomical space is one of (i) a joint, (ii) a fallopian tube, (iii) a nasal passage, and (iv) a passage in the urinary tract, (v) a neuroanatomical element, (vi) a visceral space, or (vii) a spinal space.

According to yet another implementation described in this application, there is also provided an endoscope for insertion into an anatomical space of a subject, comprising: a cannula attached at its distal end to an imaging head, the imaging head comprising:
(i) a transparent tubular shaped body having a proximal end having a curved surface, and a tubular optical guide extending from the proximal end and terminating at a distal open end of the tubular shaped body,
(ii) at least one light source disposed within the proximal end and aligned such that its illumination is directed proximally and reflected from the curved surface into the tubular optical guide,
(iii) a two dimensional detector array disposed distal to the at least one light source, and
(iv) an imaging lens assembly held by direct contact with the tubular optical guide and positioned distally to the detector array, such that it images onto the detector array, light reflected back into the imaging head,
wherein the illumination source and the detector array are aligned back-to-back such that their electronic circuits are commonly connectable.

In such an endoscope, the illumination source and the detector array may have a common power supply. In such a case, both the illumination source and the detector array may be supplied with electrical power from only a single pair of wires.

Furthermore, the electronic circuits may be adapted to modulate the illumination source with image data from the detector array, and a sample of modulated illumination may then be transmitted back down the endoscope for display of the image.

In a further exemplary implementation of these endoscopes the detector array may have an active pixelated area of size such that it will fit within the inner bore of the tubular optical guide. In that case, the non active substrate of the detector array may be held within the outer diameter of the tubular optical guide.

The illumination source in any of the above described endoscopes may be a Light Emitting Diode (LED).

The imaging head may be less than 1.8 mm. in diameter and 6 mm. in length. Additionally it may have a structure such that the illumination directed into the tubular optical guide is emitted partially distally and partially radially therefrom

BRIEF DESCRIPTION OF THE DRAWINGS

The present invention will be understood and appreciated more fully from the following detailed description, taken in conjunction with the drawings in which:

FIGS. 6A to 6B are schematic representations of cutaway sections of two different embodiments of an inflatable balloon for cytological collection such as that of FIG. 6.

DETAILED DESCRIPTION

Figure 1:
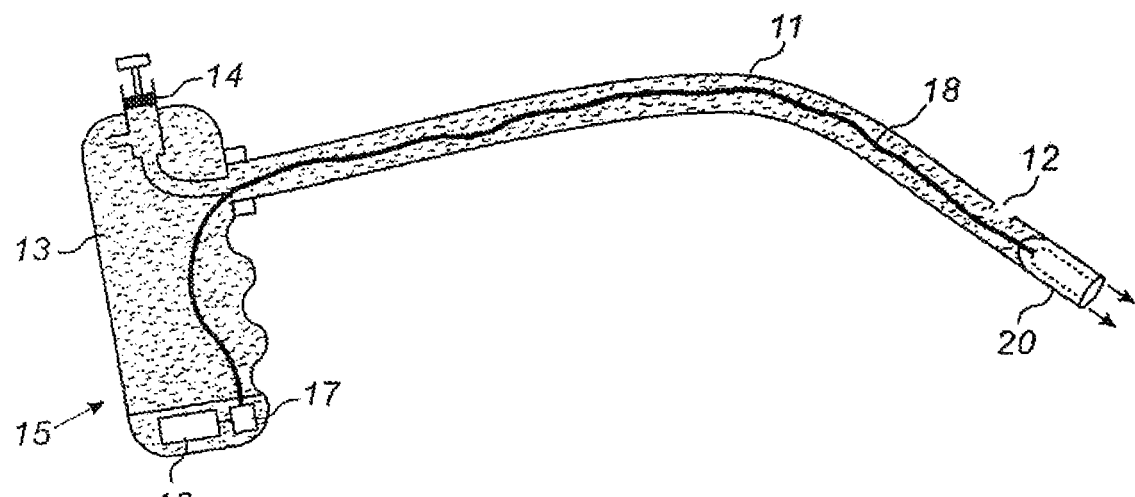
FIG. 1 illustrates schematically an exemplary miniature endoscope system according to one implementation of the present disclosure.
Figure 2A:
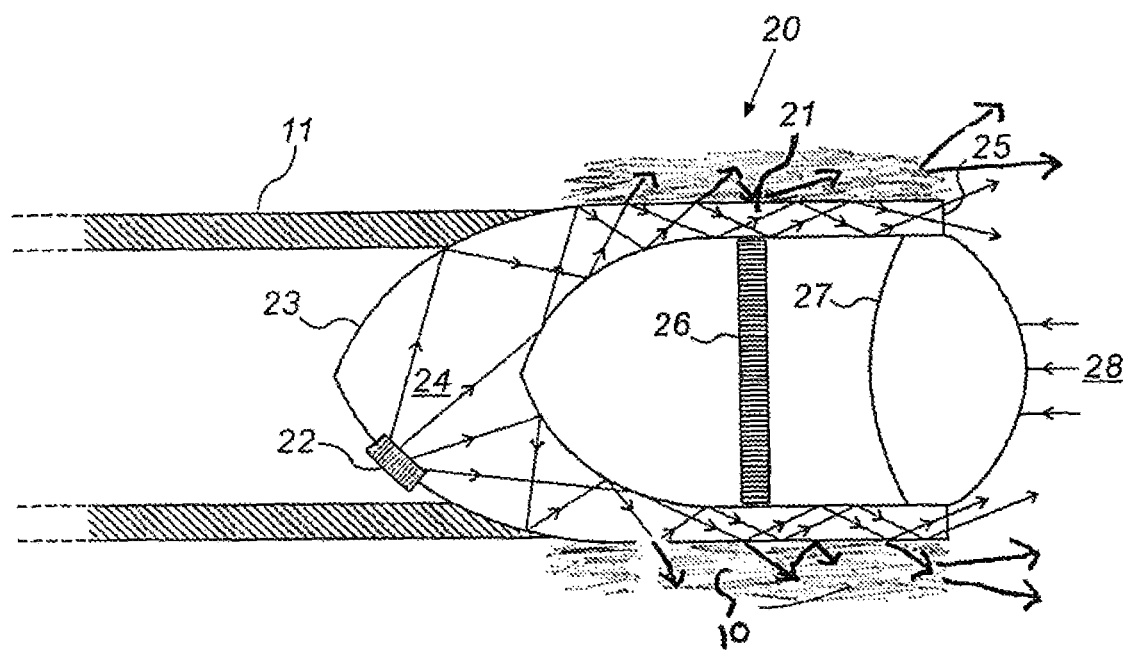
FIGS. 2A to 2E are schematic representations of cutaway sections of different embodiments of the endoscope head, showing the optical illumination and imaging system.

Reference is now made to FIG. 1, which illustrates schematically an exemplary endoscope system according to one implementation of the present disclosure, which can provide a small diameter, low-cost system. The endoscope head 20 is disposed on the end of a catheter shaft 11, which can be stiff or flexible. The head is shown in the form of an essentially cylindrical or tubular extremity having a diameter or maximum outer dimension, which need be no larger or not substantially larger than that of the catheter shaft. The internal construction of such an endoscope head is shown in FIG. 2A, hereinbelow. The catheter shaft 11 may have one or more openings 12 along its length, especially near the distal end, for injecting irrigation fluid into the anatomical space being inspected.

Because the endoscope is intended for use in small size lumens or within small volume organs or joints, the amount of irrigation fluid required is small, and in the implementation shown in FIG. 1, may be supplied by a liquid reservoir 13 such as a plastic container, with an injection mechanism 14 such as a manually operated plunger or a bellows or a balloon, for forcing the irrigation fluid out of the catheter shaft 11. This irrigation system can thus be self-contained by installation in the handle 15 of the endoscope system. The handle may thus comprise both the liquid reservoir 13, being housed entirely in the handle and the liquid injection system 14. The liquid injection system 14 may have a pump that is located entirely in the volume of the handle. This pump may be unidirectional such that it pushes liquid distally through the shaft 11 and opening 12, or may be bidirectional, such that it is also be capable of pumping liquid from a liquid source located outside of the handle liquid reservoir 13, such as a bodily lumen, in the proximal direction and into a special reservoir, such as that for cell collection. The battery 17 and any associated electronic circuitry 16 for powering the light source, the imager, and possibly also the irrigation mechanism and the wireless data transmission apparatus in the endoscope head, as to be shown in FIG. 2A, may also conveniently be installed in the endoscope handle 15, and the current transferred by wire 18 to the endoscope head 20. The injection mechanism may be actuated manually or electrically, such as from the installed battery, or from an external power source.

In the implementation shown in FIG. 1, the endoscope head 20 is connected by means of an electrical wire 18 to the handle mounted battery 17. Alternatively, if the battery is small enough, it may be positioned within the head (this implementation not shown). Signals from a head mounted camera sensor, may optionally be transferred to a wireless transmitter unit (not shown) by means of a wire connecting the camera to the wireless transmitter unit.

Reference is now made to FIG. 2A, which illustrates schematically a cutaway cross-section of an exemplary endoscope head 20 showing the component optical parts of the head, encompassing its illumination and imaging system. The endoscope head is constructed of a transparent material, such as a clear plastic or glass-like material. The head 20 may be conveniently shaped like a tube having a rounded closed proximal end with an elliptic or parabolic or circular cross section, and with the tubular wall 21, made of a light transferring material, leading to the open distal end of the endoscope head. One or more light sources, typically low-cost LED devices 22, are attached or embedded into the surface of the base 23 of the endoscope head, preferably by optical bonding, such that they emit their illumination into the transparent material of the curved base of the head, in a distal and radial distribution for illuminating the field of view. Such a distribution may be predetermined, and the endoscope head 20 may be structured to achieve this distribution, as described hereinbelow. Alternatively, the endoscope head can be formed by molding, with the illuminating devices fixed in position in the molded body.

A number of emitted rays of illumination 24 are shown in FIG. 2A. The LED or LEDs may be attached to or recessed into the curved or flat shaped section of the outer and proximal closed end of the cylinder, since in that position, they do not jut out beyond the diameter of the cylindrical housing, and therefore do not increase the overall outer diameter of the endoscope head. The inner surface of the closed tubular end of the endoscope head is also shown to be curved, typically in an ellipsoidal or paraboidal or spherical form. This base and the distal walls of the closed cylindrical head, enclose the internal volume of the head.

Selected surfaces or all of the surfaces of the light guide or cylinder wall 21, both internal and external surfaces, could be coated with a partially reflective coating, so that illumination 24 impinging on the tubular wall 21 is partially internally reflected in a distal direction down the walls of the cylindrical tube, and partially radially emitted. This radially emitted light is particularly useful for the situation shown in FIG. 2A, where the endoscope head is shown passing through an anatomical space having a region 10 radially situated to the endoscope head 20, that region being diffusive and also transmitting light entering it toward the distal end of the lumen. Such a region 10 may be located close to the endoscope head, or may be a voluminous anatomical structure such as a urinary bladder, uterus, or knee joint, in which the walls of the structure may be situated 10 to 30 mm. from the endoscope head outer walls. The beneficial nature of the radially emitted light is somewhat different in these two cases. When the endoscope head is passing through an anatomical lumen with walls close to the head as shown in FIG. 2A, the effect generated is one of decreasing the forwardly projected illumination emitted from the tubular wall 21, and increasing the forwardly projected illumination 25 through the tissue of the lumen surrounding the head. This distally redistributed light assists in producing a more uniform distribution of light to the field of view. On the other hand, if the endoscope head is passing through a voluminous organ with walls not in direct contact or not close to the endoscope head, then the effect of the radially emitted light, is to increase the general illumination inside the organ, with commensurate advantages in such illumination.

Generally, the inner surface of the tubular wall 21, that makes contact with the lens assembly 27 and the detector array 26, should be fully reflective such that illumination 24 does not pass out of the cylindrical wall into the inner volume of the endoscope head where the detector array 26 is located. To achieve an advantageous distribution of radially and distally emitted light, a number of different structures may be proposed. The simplest structure has a partially reflective coating on the outer surface of the tubular wall 21. This coating then partially radially transmits light incident on it, and partially reflects light incident upon it, back into the tubular wall 21. The percentage of light transmitted radially outwards and that reflected down the tubular wall 21 can be selected according to the reflectivity of the coating. In a second implementation, a diffusive coating substance or surface treatment may be used for the outer surface of the tubular wall 21 such that the outer surface promotes radial light dispersion along the tubular wall light-guide by scattering, reducing axial flux at the distal end 25 of the endoscope head. Additionally, the proximal end 23 of the light-guide 21 may have a diffusive coating on its inner surfaces, which affects the dispersion of light 24 exiting from the light source 22, at the proximal end of the endoscope head. A type of surface treatment, coating, or a coating with a known refractive index may be chosen according to the desired illumination of the anatomical space, taking into account the shape of the proximal end of the endoscope head, the position of the light source 22, and the shape, size and light diffusing properties of the anatomical region to be explored. For example, the position and angle of the light source shown in FIG. 2A, in combination with the shape of the endoscope head shown in this drawing, may result in light impinging on the surfaces of the tubular wall 21 at angles that promote internal reflection within the tubular wall 21. In such a case, a coating with a relatively higher refractive index than the material of the tubular wall 21 may be used to promote radial emission of light. When the endoscope is located in a large cavity, such as a urinary bladder, radial emission of light from the endoscope head acts differently, by providing overall illumination to the inside of the cavity, and such a coating may be used for this purpose as well. On the other hand, if the endoscope is passing through a small space within a joint, the diffusive portion 10 of the anatomical region does exist, either due to lack of space radial to the endoscope head or due to lack of diffusive properties of the anatomical material surrounding the head. If the diffusive portion 10 is not present, such as in a situation where there is no tissue to diffuse the light, for example, due to the presence of an opaque bone structure, the radially emitted light may be redirected, such as by a bone structure, within the tubular wall 21 in the distal direction. Thus, if it is known that such a situation is likely to be encountered, an efficiently structured endoscope should have a coating with a relatively low refractive index on the outer surface of the tubular wall 21 to encourage distal emission of light, since only this distally emitted light will be used to illuminate the region of interest.

The radially emitted light, after exiting the endoscope head, is either diffused within the tissues of the anatomical region 10 or scattered by the outer surface of the tubular wall 21, or both. The tubular wall 21 may have a structured or surface treated outer surface to encourage such scattering. Ultimately, the illumination is emitted from the distal annular end wall 25 and from the distal portion of the anatomical region 10 to illuminate the field of view in front of the endoscope head. This distal annular end wall 25 is shown flat in FIG. 2A, but could also be curved or tilted. This scattering or diffusion allows a portion of the radially emitted light to be ultimately directed distally, such that the distribution of light emitted by the endoscope head is not limited that resembling a Gaussian function, and over-illumination of the centrally located portion of the area of illumination is prevented. This arrangement results in a more widely spread distribution of light and in good illumination over the area of examination.

In addition to the walls having a predetermined reflectivity, the position and orientation of the LED source 22 or sources, and the structure of the internal base surface of the endoscope head is shaped so as to ensure that an advantageous proportion of the incident illumination on the tubular wall 21 is partially internally reflected to ultimately reach the distal end of the endoscope head 25. The remaining portion of light from the LED source 22 is emitted radially out of the outer wall of the body. The cylinder wall 21 thus acts as a light waveguide from the source or sources 22 to the annular emitting aperture 25.

The optical imaging system should include a miniature imaging sensor integrated into the endoscope head, located distally to the light source. The endoscope head should also contain a lens assembly 27, generally having one or more imaging lenses located distally to the imaging sensor. The light may be generated by one or more LEDs, located at the proximal end of the head, and is directed internally along the tubular wall of the head, which also functions as the lens holder barrel. Since the lens assembly 27 is held in direct contact with the tubular wall 21, there is no need for a separate lens holder, and the diameter is not increased beyond that of the lens assembly 27 and the tubular wall 21.

The angle at which the light is directed from the LED(s) towards the tubular wall may be chosen to be less than the critical angle with respect to the normal to the tubular wall surface, and thus one which will result in partial internal reflection. The wall of the head 21 is made of light transferring material and the walls 21 may have a partially reflective coating applied to allow a desired partial internal reflection and partial external transmission. Using the walls of the device and the anatomical space proximal to the imaging head for transferring the light from the proximal end of the head to the distal field of view, reduces the endoscope diameter, because it eliminates the prior art need for an additional light transfer element, such as an optical fiber, or the use of LED(s) placed peripherally to the optical system, or the use of a lens holder that does not transmit the illuminated light, thus consuming space and increasing the diameter of the endoscope beyond that dictated by the camera. Integration of the light source 22 into the diameter of the endoscope head by placing the LED(s) 22 close to the longitudinal axis of the endoscope head and by means of using the wall 21 of the endoscope head, or part of it, as a light-guide, reduces the overall diameter of the endoscope head 20, which is generally the part of the endoscope with the largest diameter.

It is to be understood that although the endoscope body is described in this implementation as being cylindrical or tubular, usually understood to having a circular cross section, this being the most cost-effective and convenient form to use, the invention is not intended to be limited to a pure right circular cylindrical shape, but that any other suitable shape, such an oval or elliptical shaped cylinder, could also be used. The term cylinder, and derivatives, such as cylindrical, or tubular, as recited and as claimed in this application, are not therefore intended to be limited to having circular cross sections, but can be understood to have other suitable cross sections also.

An imaging sensor 26, such as a CMOS detector array, is shown disposed inside the central volume of the endoscope head near the proximal end, with at least one imaging lens 27 disposed distally of the sensor array 26, such that illumination 28 reflected from parts of the imaged organ or lumen within the field of view of the emitted illumination, is focused by the imaging lens 27 onto the sensor array 26. The imaging system thus provides an image of the region distally in front of the endoscope head, having high image quality and good visualization of the examined organ, because of the more uniform illuminations generated by presently described endoscopes. The imaging lens 27 may advantageously be located at the tip of the cylinder at the very proximal end of the endoscope head. The lens design provides an atraumatic distal end, having a curved shaped structure that avoids damage to anatomical structures that come into engagement with it during a procedure. Furthermore, the transparent material of the endoscope head may be selected to have a certain limited level of flexibility, such that if the head encounters an obstruction in the lumen into which it is being inserted, it will deform slightly rather than undergoing breakage, which could be harmful to the patient. However, the level of flexibility must be such that the mutual position of the lenses and the imaging sensor are not moved to such an extent that the image quality is degraded.

The endoscope head 20, is attached to the distal end of the catheter shaft 11 such that it can be maneuvered within the patient's body to the site to be inspected. The arrangement whereby the light source 22 is contained within the diameter of the sensing element enables a substantial reduction in head diameter to be achieved. The size of the head may be 1.8 mm. in diameter by 6 mm in length, but even smaller head units can be envisaged as the size of the imaging arrays becomes smaller.

Figure 2B:
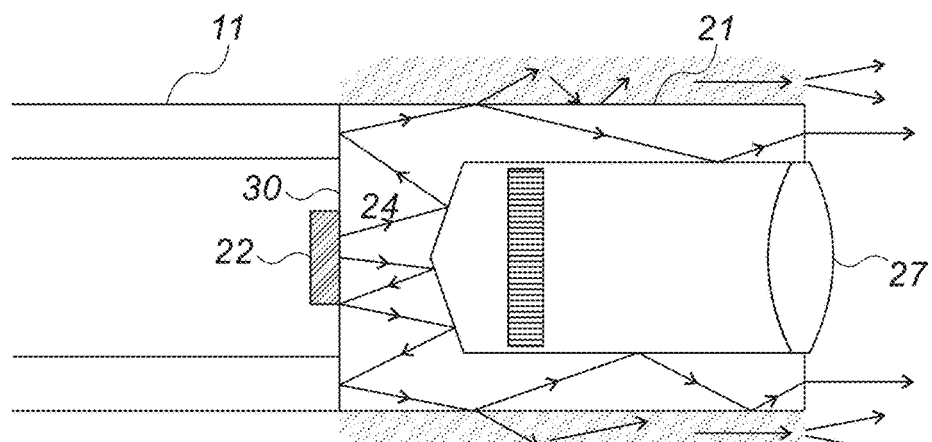

Reference is now made to FIG. 2B, which illustrates schematically an alternative arrangement for the mounting of the illumination source or sources 22 in the head, using a flat-backed 30 housing cavity, to simplify the mounting. In this implementation, coatings may be used for one or more surfaces of the wall 21 that have a reflectivity that allows the emitted light 24 to be distributed both radially from the outer surface of the walls 21, and distally from the tubular output wall 21.

Figure 2C:
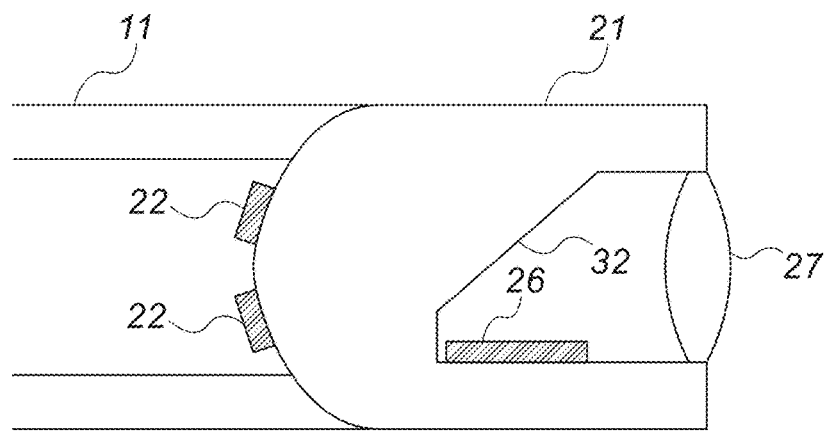

Reference is now made to FIG. 2C, which illustrates schematically an alternative position for mounting the detector array 26, using a beam-bending surface 32. By using the length of the head cavity to locate the detector array, this implementation may enable the use of a larger detector array having a larger number of pixels for increased image resolution. The beam-bending mirror surface can conveniently be formed as a 45° aligned base wall 32 of the internal cavity of the head, with the mirror property defined by means of an internal coating.

The layouts of the arrangements of FIGS. 2B and 2C are being brought as examples of alternative implementations of the arrangement of FIG. 2A, and are not intended to be exhaustive. The inventive aspect of all of these implementations is that the head of the endoscope is designed to enable the illumination to be emitted in an advantageous distribution both radially and from the distal end, without the illumination source essentially protruding beyond the outer dimension of the head, as determined by the maximum size of optical component installed therein.

Figure 2E:
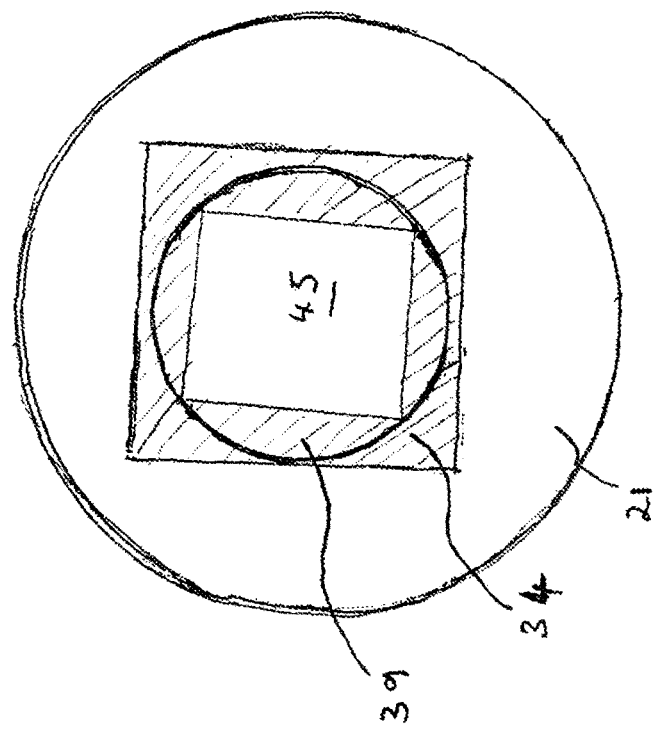
Figure 2D:
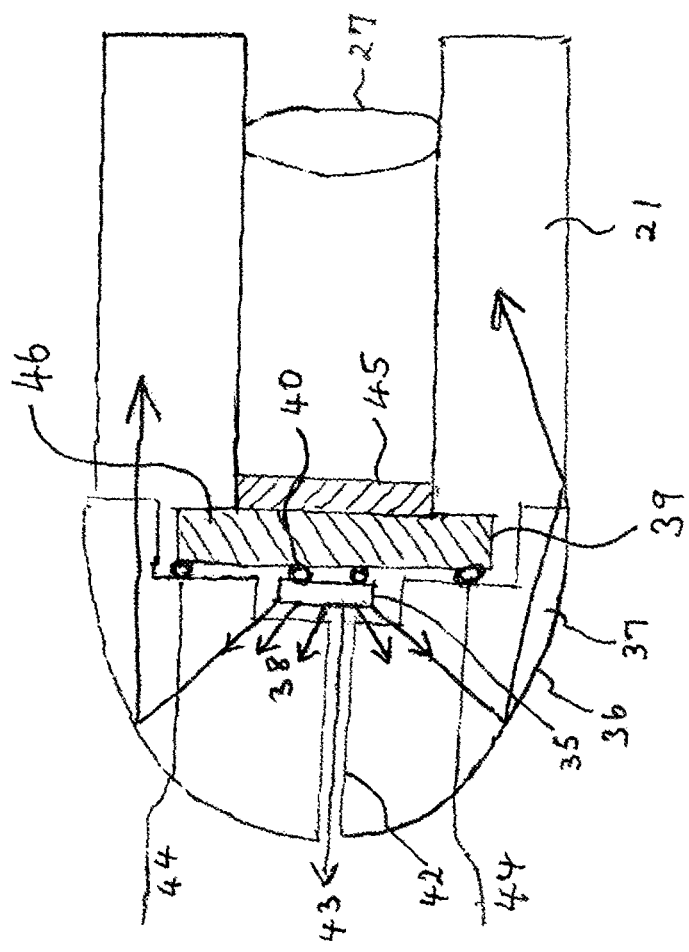

Reference is now made to FIG. 2D, which illustrates a further alternative arrangement for the illumination source and the imaging detector array, having a number of advantages which makes this arrangement particularly advantageous for use in the miniature endoscopes of this disclosure, both in ease and cost of manufacture. The arrangement shown in FIG. 2D is also designed to direct the illumination down the tubular light guide, in order to project the illumination distally from the endoscope head. However, it differs from the embodiments shown in FIGS. 2A to 2C in that the LED source 35 is located in a novel position directing the illumination 38 backwards in the proximal direction. The illumination is then reflected on the curved outer surface 36 of the transparent housing element 37 back into a forward direction and down the light guide 21. The reflection can be implemented either by total internal reflection or by silvering on the outer surface, The advantage of this location is twofold:

(a) Since the LED illumination source is then back-to-back with the image sensor drive circuits 39, it is possible to provide electrical connection between them by means of common vias and ball connectors 40, as are known in the microelectronic fabrication industry, thereby simplifying construction, since power to the LED source can be supplied from the same power supply as that providing power to the CMOS image sensor. Another optional possibility is that the LED source can be connected and controlled directly by the CMOS, such as is performed in ALC (Automatic Light Control) circuits.

(b) It is possible to transmit the image data from the output of the image sensor optically, by a novel method of modulating the LED output illumination with the picture data from the image sensor. Since the picture data is generated at a high frequency and can be a small modulation level on the general DC illumination of the LED, the illuminating function of the LED is not affected by this imposed modulation. On the other hand, it is possible to transmit the picture data optically by extracting a small sample of the LED illumination, and transmitting it back approximately down the endoscope to a receiver in the handle, where the modulation can be extracted and the picture data re-constructed. Since the LED device is facing in the proximal direction, this is optically very simple to achieve. In the implementation shown in FIG. 2D, this is achieved by use of a small transmissive tunnel 42 in the curved transparent end element, such that illumination 43 with the image information impressed on it, is transmitted back to the handle and its associated control and monitor circuits, without being reflected distally along with the main portion of the LED illumination. Using this arrangement of common power circuits for the imaging sensor chip 39 and the LED 35 can minimize the number of wires 44 required to operate the detector and LED source to only two, this being a substantial saving in design and manufacturing of the endoscope head.

Reference is now made to FIG. 2E, which illustrates a further advantage used in the construction of any of the implementations of FIGS. 2A to 2D, but which is most simply illustrated in the implementation of FIG. 2D. FIG. 2E shows an end-on view of the image sensor 39 disposed within the tubular light guide 21. As is observed in FIG. 2D, the substrate of the image sensor is larger than the light-sensitive pixelated region 45 for imaging the light collected by the lens. This construction is inevitable in CMOS manufacturing techniques, since it is impossible to produce a pixelated light-sensitive area extending right out to the edges of the substrate on which the sensor array is constructed. Referring back again to FIG. 2D, the inactive part of the substrate of the CMOS image sensor is recessed into a space 46 behind the light guide, such that the active pixelated area 45 on the front of the image sensor fills the entire optical bore of the endoscope head. By this means, the optically inactive substrate borders do not cause any increase in the necessary diameter of the endoscope head, since it is within the outer diameter or close to the outer diameter of the light guide. The corners 34 of the substrate are used to affix the imaging device in position, and are held in place by the tubular light guide. Thus, those corners do obstruct a portion of the light transmission path down the light guide 21, but the percentage of blocking is negligible, when considered in the context of the reduction in head diameter thus achieved, which is the most important parameter considered in the construction of the device.

Figure 3:
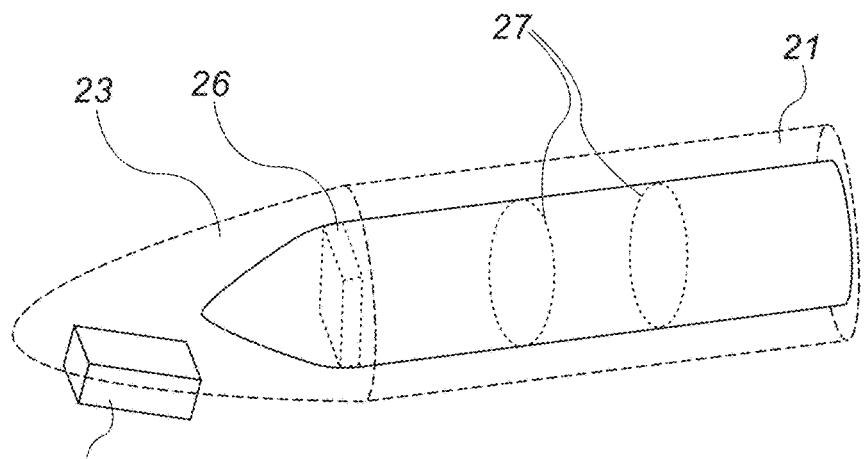
FIG. 3 is an isometric view of an exemplary endoscope head such as that of FIG. 2A.

Reference is now made to FIG. 3, which is an isometric view of an exemplary endoscope head, showing the transparent body 23, a LED illumination source 22, an imaging sensor 26 and a lens assembly 27 mounted within the transparent barrel 21, and their mutual positions within the head. Although in this figure two lenses are shown, alternative implementations may have a lens assembly 27 with more than two lenses.

Figure 4:
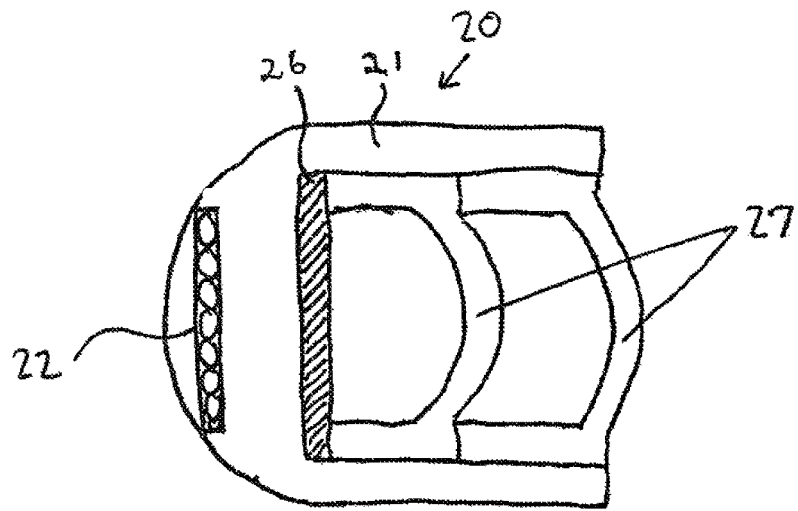
FIG. 4 is a schematic representation of an endoscope head having a wafer level optics lens assembly.

Reference is now made to FIG. 4, showing an exemplary endoscope head constructed using wafer level optics technology. To further decrease the production cost of the endoscope head, the lens assembly 27 and the detector array 26 may be produced using such a wafer level optics element, such as could be cut from a substrate on which layers of printed lenses and a detector array are formed. The lens assembly fits into the tubular wall 21, which act as an illumination guide for the light emitted from the LED 22, and also stabilizes the head structure during medical procedures of insertion, maneuvers and manipulation in a bodily organ.

In an advantageous implementation, the endoscope may additionally be used for detaching cells from a region being investigated and then sampling such detached cells by flushing the region with a liquid, and then pumping out the liquid with the cells to be investigated through the orifice 12, or through another orifice in the catheter. The flushing may be performed using the irrigation system located in the endoscope handle, as shown in FIG. 1. Such a cytological pump can be used in gynecology, for instance, for the detection of ovarian cancer. Such a cytological application must include means of detaching and collecting the cells to be analyzed. An exemplary schematic representation of a handle used for such cytological implementations, including the required pumps and tubing, will be shown in FIG. 7.

Figure 5:
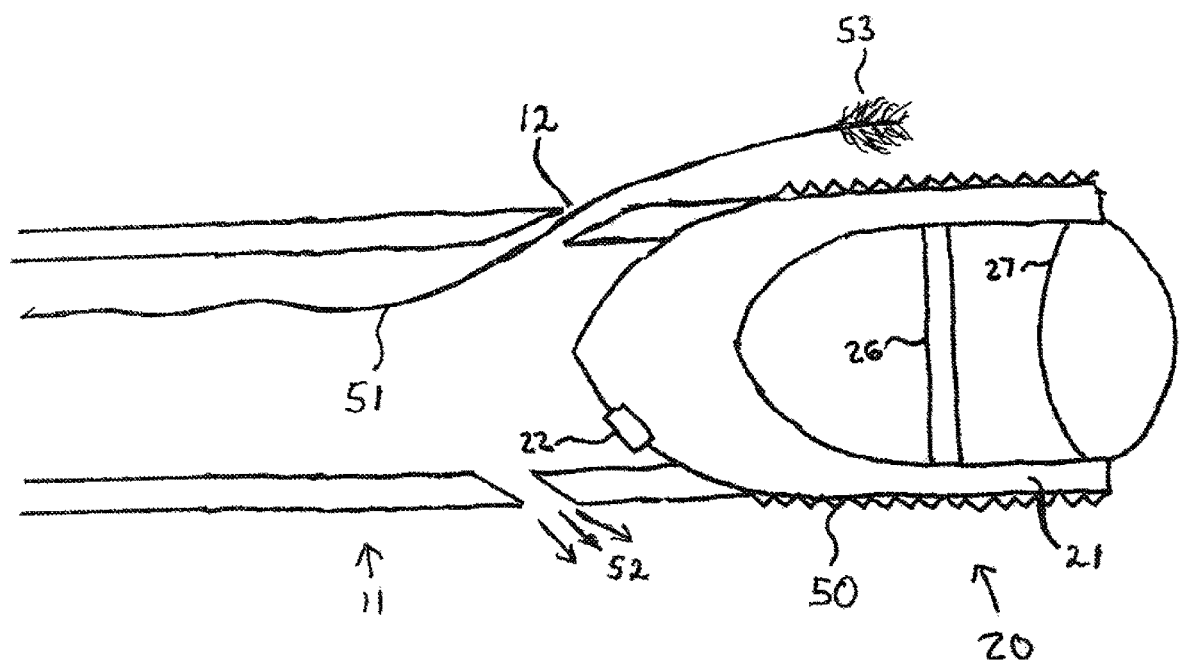
FIG. 5 is a schematic representation of an endoscope having an imaging head with a structured outer surface for cytological collection, and oriented holes for irrigation and guide-wire passage, the guide wire also being adapted for use in cytological collection.

Reference is now made to FIG. 5, showing a schematic representation of a miniature endoscope having an imaging head 20 with a structured outer surface 50 for detaching such cells to be collected. As the head 20 advances inside an anatomical space, the structured outer surface 50 detaches cells from the passage through which it is moving. In the implementation shown in FIG. 5, the outer walls of the endoscope head 21 have a structured surface, so that the structured outer surface collects cells found, for instance, in the mucosa of the organ or among the cilia on the inner walls of the fallopian tubes. In this implementation, the small diameter of the endoscope head is not significantly increased by the structured surface 50. Although the structured surface shown in FIG. 5 is made up of cone-shaped protrusions, any suitable structuring, such as a jagged, toothed, 63 rough 64, hairy or swab-like surface 62 may be used. The light source (or sources) 22 provides illumination into the tubular wall 21, where it is distally and radially emitted, as shown in FIG. 2A, and reflected illumination is directed toward the lens assembly 27 where it is focused onto the detector array 26. The structured surface is made of a material such that it supports the advantageous light distribution and allows for both radial and distal emission of light from the endoscope head 20. If the material of the structured surface is very reflective, it may be used to cover only a portion of the endoscope head, so as to allow the desired partial radial emission of light. Furthermore, although the structured surface has been shown in FIG. 5 covering only the imaging head, according to further implementations, this structure can be applied to part of the catheter outer wall 11.

Reference is now made in FIG. 5 to the arrangement of irrigation hole or holes 12 at the distal end of the endoscope, which enable more specific direction of the irrigating fluid, and also facilitate the use of the endoscope with a guide wire. By producing the irrigation holes at an acute angle to the axis of the endoscope tube, the ejected irrigation or flushing fluid 52 is directed in a forward direction, which is a preferred direction for efficient irrigation and to flush debris and opaque fluids from the region which the imaging camera is to view. However, another advantage of this orientation of the irrigation holes is that the exit of a guide wire 51 passing down the endoscope bore is facilitated. Such a previously inserted guide wire can be used in its conventional function of guiding the endoscope to the target desired or in the direction desired, or, if a collection swab 53 is attached to the end of the guide wire 51, it can be used to collect and withdraw cell samples from the inside of the lumen or organ or anatomical space into which the endoscope has been inserted.

Figure 6:
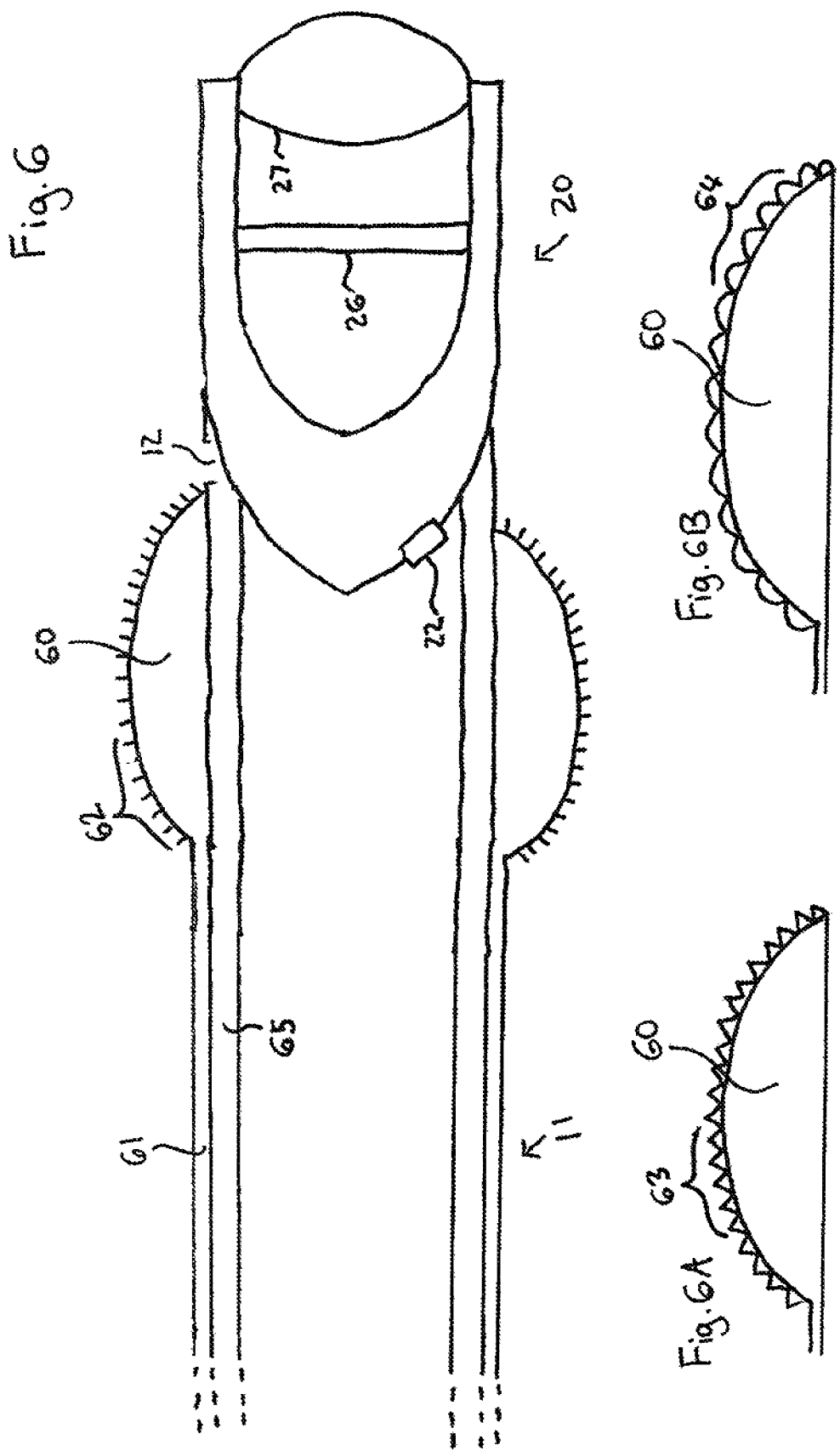
FIG. 6 is a schematic representation of an exemplary endoscope having an inflatable balloon for cytological collection.

Reference is now made to FIG. 6, showing a schematic representation of another exemplary endoscope having an inflatable balloon 60 for cytological collection. The balloon 60 is shown located peripheral to the catheter and is adapted to make contact with the walls of an anatomical space when inflated in order to detach cells. The balloon 60 can be inflated via a balloon pump located in the handle, which may be the injection mechanism 14 shown in FIG. 1, or a separate pump (separate pump not shown in FIG. 1) that pushes gas, or more usually liquid, down the tube structure 61 located in the cannula shaft 11, when the endoscope head reaches its desired location. The inflatable balloon 60 has a rough surface 62 to promote cell collection from the walls of the anatomical space that the endoscope is exploring. This exemplary surface 62 has bristles adapted to collect cells from the walls of an anatomical space. Reference is now made to FIGS. 6A and 6B, showing schematic representations of cutaway sections of two different exemplary embodiments of an inflatable balloon for cytological collection such as that of FIG. 6. The balloon shown in FIG. 6A has a sharp toothed external surface 63, and the balloon shown in FIG. 6B has a rugged external surface 64. Additional implementations may have a balloon with a round toothed, rough, hairy or swab-like surface. A balloon is particularly advantageous because its outer surface conforms to the walls of the organ or lumen in which the endoscope is located as the endoscope moves through a bodily lumen, providing a large surface area of contact for maximal cell collection. The inflation or filling pressure should be controlled in order to provide an efficient cell collection procedure without danger of damage to the subject by over-inflation or over filling. Both the balloon and structured surface embodiments allow for simpler methods of cell collection than the prior art method of passing a swab down the working channel of the endoscope. As shown previously in FIG. 2A, the light source 22 provides illumination into the tubular wall, where it is distally and radially emitted, as shown in FIG. 2A, and reflected illumination is directed toward the lens assembly 27 where it is focused onto the detector array 26.

Figure 7:
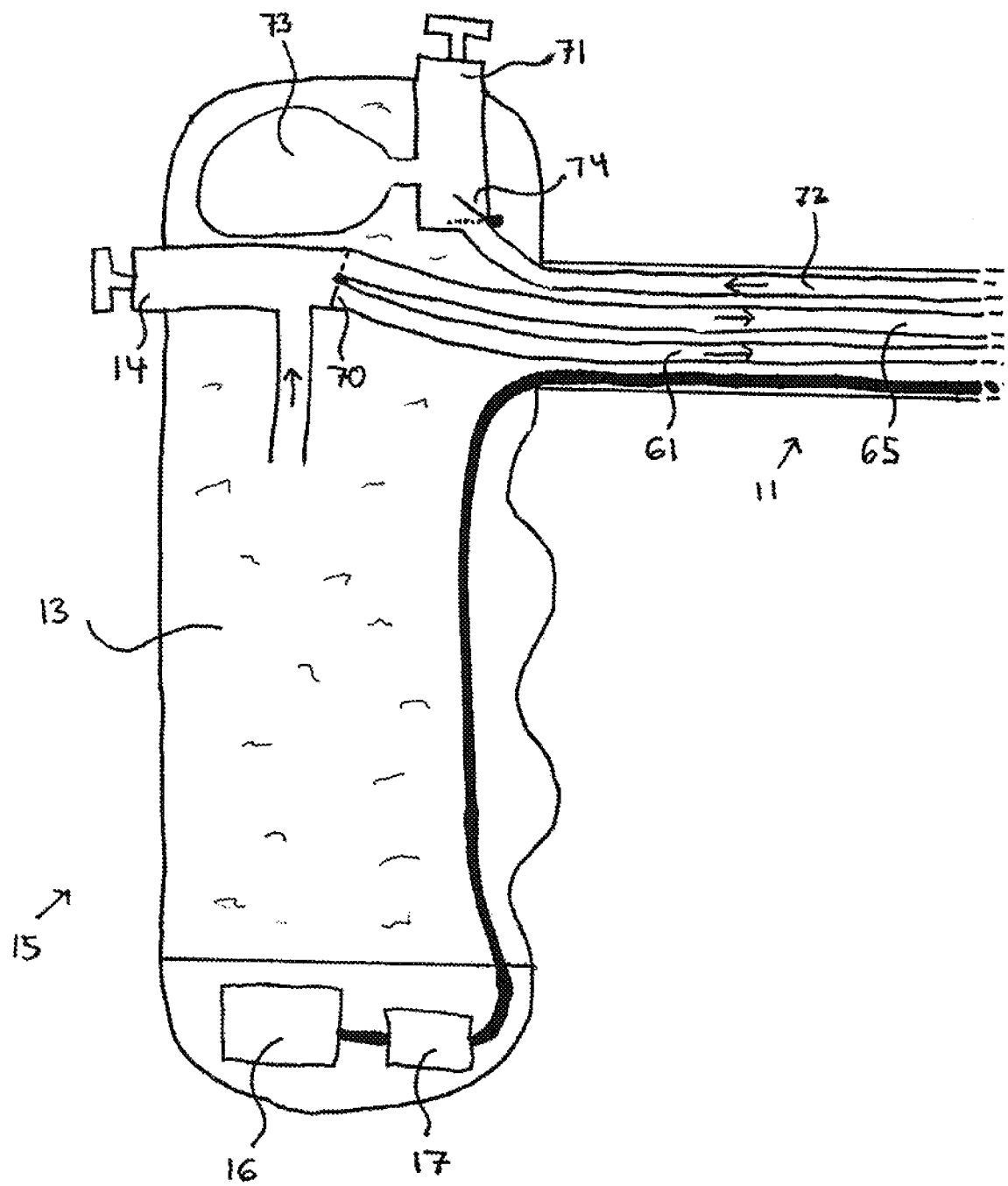
FIG. 7 shows a schematic representation of an exemplary miniature endoscope handle, incorporating a mechanism for withdrawing fluid for cytological collection

Reference is now made to FIG. 7, which shows a schematic representation of an exemplary miniature endoscope handle, for use with an inflatable balloon for cytological collection, as shown in FIG. 6. Liquid injection pump 14 is for ejecting liquid from the device through orifice 12 (shown in FIG. 1), and a separate liquid withdrawal pump 71 is shown for withdrawing liquid from an anatomical region through an orifice in the catheter and into the cell collection reservoir 73 located in handle 15 of the device. The cannula 11 houses three separate tube structures: tube structure 61 for filling of the balloon 60, tube structure 65 for ejecting liquid out of opening 12 into the anatomical space, and tube structure 72 for withdrawing liquid containing cells from the anatomical space proximal to the endoscope head into a cell collection vessel 73. A one-way flap 74 is provided to prevent collected cells from leaking back out of the cell collection vessel 73. The arrangement of the tube structures within the cannula may be any suitable arrangement that allows for liquid to flow in the directions shown as arrows in FIG. 7. For example, shaft 61 for use in balloon inflation may be located towards the outer surface of the cannula so that it is proximal to the balloon. The cannula 11 has sufficient structural rigidity to house all of these tube structures such that as the cannula is maneuvered through the anatomical space, the flow of liquid through the tube structures is not adversely affected. The liquid injection mechanism 14, which may be manually operated, pumps liquid out of liquid reservoir 13 through an inflow tube and towards valve 70. After passing through valve 70, liquid continues in the distal direction down the catheter 11. Valve 70 may comprise two separate flaps to alternately block tube structure 61 or tube structure 65, such that liquid will be injected either into the balloon or out of opening 12, according to the needs of the user. It is to be understood that a similar handle structure may be used with the cytological implementation of FIG. 5, but this alternative handle would only require tube structures 65 and 72, since there is no balloon in this implementation. As such, valve 70 would not be necessary in the FIG. 5 implementation.

It is appreciated by persons skilled in the art that the present invention is not limited by what has been particularly shown and described hereinabove. Rather the scope of the present invention includes both combinations and sub combinations of various features described hereinabove as well as variations and modifications thereto which would occur to a person of skill in the art upon reading the above description and which are not in the prior art.

The invention claimed is:

1. An endoscope for insertion into an anatomical space of a subject, comprising:
    a handle comprising (i) a liquid reservoir, housed entirely in said handle and (ii) a liquid injection system comprising a pump;
    a cannula attached at a proximal end to said handle, said cannula having at least one opening through which liquid from said reservoir can be ejected from said cannula; and
    an imaging head, having an essentially closed proximal end attached distally to an end of said cannula, said imaging head comprising:
        a transparent tubular wall extending distally from said essentially closed proximal end;
        at least one light source associated with said essentially closed proximal end, the at least one light source being disposed such that its light is directed into said transparent tubular wall, and said at least one light source being disposed radially inwards of outer dimensions of said transparent tubular wall;
        a two dimensional detector array disposed inwardly of an inner surface of said transparent tubular wall and distal to said at least one light source; and
        an imaging lens assembly held by direct contact with said transparent tubular wall and positioned distally to said detector array, such that it images onto said detector array, light reflected back into said imaging head,
    wherein said imaging head has a structure such that said transparent tubular wall is an outermost element of a distal end of the endoscope, and said illumination directed into said transparent tubular wall is emitted partially distally and partially radially outwards therefrom.

2. The endoscope according to claim 1, wherein said pump is housed entirely in said handle.

3. The endoscope according to claim 1, wherein said partially distally emitted and partially radially emitted illumination from said transparent tubular wall have a distribution which illuminates said anatomical space both distally and laterally.

4. The endoscope according to claim 3, wherein said distribution is achieved, at least in part, by having optically diffusive coatings on at least parts of an outer surface of said transparent tubular wall.

5. The endoscope according to claim 1, wherein an outer surface of said transparent tubular wall has a partially reflective coating that has a reflectivity chosen to achieve a predetermined proportion of light to be emitted radially and a predetermined proportion of light to be emitted distally.

6. The endoscope according to claim 1, wherein said pump is adapted to eject liquid from said reservoir through said cannula and out of said at least one opening in an outer wall of said cannula.

7. The endoscope according to claim 1, wherein said transparent tubular wall is a barrel of said lens assembly.

8. The endoscope according to claim 1, wherein a distal lens of said lens assembly is designed such that a distal surface is convex shaped such that it reduces trauma to the anatomical space through which said endoscope is passed.

9. The endoscope according to claim 1, wherein said imaging head is less than 1.8 mm in diameter and less than 6 mm in length.

10. The endoscope according to claim 1, further comprising a cytological collection element associated with said imaging head, that is adapted to detach cells from said anatomical space in which said imaging head is situated.

11. The endoscope according claim 10, wherein said handle further comprises a liquid withdrawal mechanism adapted to withdraw liquid in a proximal direction through said cannula.

12. The endoscope according to claim 11, further comprising a cell collection vessel within said handle to collect liquid withdrawn from said liquid withdrawal mechanism.

13. The endoscope according to claim 10, wherein said cytological collection element is disposed on the end of a guide wire deployed from an irrigation opening in an endoscope cannula wall.

14. The endoscope according to claim 10, wherein said cytological collection element is a structured surface on an outer surface of at least one of: said transparent tubular wall, at least part of said cannula, or an inflatable balloon.

15. The endoscope according to claim 14, wherein said structured surface is at least one of (i) rough, (ii) jagged, (iii) toothed, and (iv) hairy.

16. The endoscope according to claim 10, wherein said cytological collection element is an inflatable balloon having a rough or toothed external surface.

17. The endoscope according to claim 1, wherein said handle further comprises a battery and electronic circuits for operation of the endoscope.

18. The endoscope according to claim 1, wherein said image head is no larger or not substantially larger than said cannula.

* * * * *